(12) United States Patent
Bosworth, Sr. et al.

(10) Patent No.: US 7,311,461 B2
(45) Date of Patent: Dec. 25, 2007

(54) LIQUID CONTAINER AND METHOD OF USE

(75) Inventors: John O. Bosworth, Sr., Upper Nyack, NY (US); John O. Bosworth, Jr., Upper Nyack, NY (US); Vladmir Bogin, Longview, WA (US)

(73) Assignee: Ingen Solutions Group, LLC, Upper Nyack, NY (US)

( * ) Notice: Subject to any disclaimer, the term of this patent is extended or adjusted under 35 U.S.C. 154(b) by 74 days.

(21) Appl. No.: 10/506,953

(22) PCT Filed: Mar. 7, 2003

(86) PCT No.: PCT/US03/07143

§ 371 (c)(1),
(2), (4) Date: Sep. 7, 2004

(87) PCT Pub. No.: WO03/075710

PCT Pub. Date: Sep. 18, 2003

(65) Prior Publication Data

US 2005/0105957 A1    May 19, 2005

Related U.S. Application Data

(60) Provisional application No. 60/406,287, filed on Aug. 28, 2002, provisional application No. 60/363,000, filed on Mar. 8, 2002.

(51) Int. Cl.
*B43K 5/00* (2006.01)

(52) U.S. Cl. ............... 401/199; 401/126; 401/21
(58) Field of Classification Search ............ 401/6–8, 401/21, 23, 126, 196, 198, 199, 202, 207
See application file for complete search history.

(56) References Cited

U.S. PATENT DOCUMENTS

| | | | | | |
|---|---|---|---|---|---|
| 2,097,496 | A | * | 11/1937 | Lunzer | 401/196 |
| 3,199,754 | A | * | 8/1965 | Sorensen | 224/222 |
| 4,111,567 | A | * | 9/1978 | Berghahn et al. | 401/202 |
| 4,341,482 | A | * | 7/1982 | Wollensak | 401/199 |
| D288,743 | S | * | 3/1987 | Taylor | D3/226 |
| 4,712,571 | A | * | 12/1987 | Remz et al. | 401/199 |
| 4,821,748 | A | * | 4/1989 | Reas | 401/205 |
| 5,087,144 | A | * | 2/1992 | Wada et al. | 401/199 |
| 5,172,683 | A | * | 12/1992 | West | 126/263.05 |
| 5,215,379 | A | * | 6/1993 | Pickard et al. | 224/222 |
| 6,464,420 | B2 | * | 10/2002 | Brunetti | 401/202 |
| 6,626,334 | B2 | * | 9/2003 | Ewing | 401/202 |
| 6,662,986 | B2 | * | 12/2003 | Lehtonen | 224/675 |

* cited by examiner

*Primary Examiner*—Khoa D. Huynh
(74) *Attorney, Agent, or Firm*—John H. Crozier

(57) ABSTRACT

In a preferred embodiment, a liquid container (30, 200), including: a bottom (32, 230; a reservoir tube (34, 232) disposed in the bottom (32, 200); a capillary (38, 212) disposed in contact with the reservoir tube (34, 232); a middle portion (36, 210) disposed on the bottom (32, 200); and the capillary (38, 230) having an upper portion (62, 222) extending from an upper opening of the middle portion (36, 210).

16 Claims, 8 Drawing Sheets

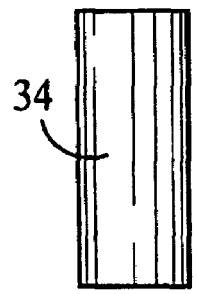
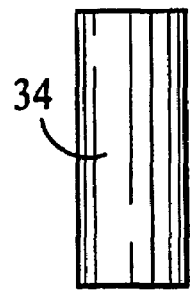
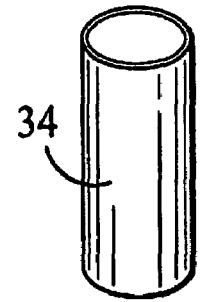
FIG. 6   FIG. 7   FIG. 8
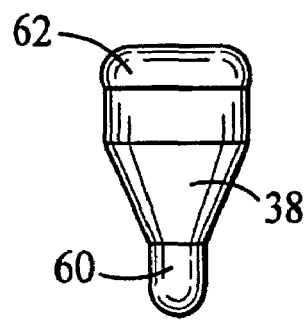
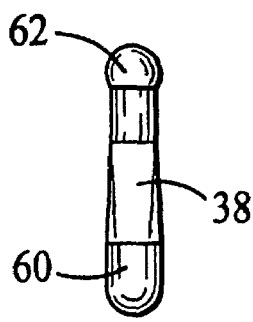
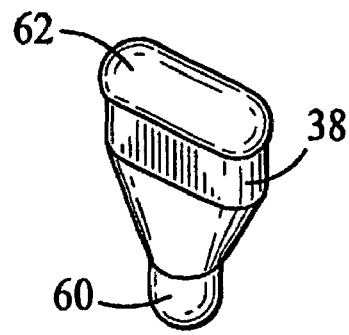
FIG. 9   FIG. 10   FIG. 11

LIQUID CONTAINER AND METHOD OF USE

CROSS-REFERENCE TO RELATED APPLICATIONS

The present application is a 35 USC 271 of PCT/US03/07143, filed Mar. 7, 2003, and titled LIQUID CONTAINER AND METHOD OF USE. Benefit is claimed of the filing dates of U.S. Provisional Applications, Ser. Nos. 60/363,000, filed Mar. 8, 2002, and 60/406,287, filed Aug. 28, 2002, both titled LIQUID CONTAINER AND METHOD OF USE.

TECHNICAL FIELD

The present invention relates to liquid containers generally and, more particularly, but not by way of limitation, to a novel liquid container and method of use.

BACKGROUND ART

Liquid containers are available in a wide variety of configurations. The present invention addresses two uses of liquid containers. One is the use of a liquid container for sterilization, such as sterilizing the diaphragm and chestpiece and/or earpieces of a stethoscope, or acupuncture needles, or diabetes needles, for example. The other is the use of liquid container for the application of a liquid cosmetic or other liquid material, such as nail polish remover, a cosmetic, or an insect repellant, for example.

The manufacturers of stethoscopes recommend that stethoscopes be disinfected often to prevent possible cross-contamination between patients. Unfortunately, the means to disinfect stethoscopes are not readily available to the user of the stethoscope and, as a result, stethoscopes often are not disinfected for fairly long periods of time, with the concomitant possibility of cross-contamination. Acupuncture needles and diabetes needles are obviously in need of sterilization between uses, particularly if a different person is to use the needles.

Liquid cosmetics are often applied by shaking a small quantity from a container with a narrow opening or by spraying from a container. In either case, such application is relatively messy and can waste the liquid. The same is true of other liquid materials.

Accordingly, it is a principal object of the present invention to provide a liquid container for a disinfectant, such as alcohol, or to provide a container for another type of liquid material, such as a cosmetic, that is easy to use.

It is a further object of the invention to provide such a liquid container and method of use that is economical.

It is an additional object of the invention to provide such a liquid container that can be economically manufactured.

It is another object of the invention to provide such a liquid container that can be conveniently mounted.

It is yet a further object of the invention to provide such a liquid container that can be unobtrusively mounted on a stethoscope.

It is yet an additional object of the invention to provide such a liquid container and method of use that conserve the contents of the liquid container.

Other objects of the present invention, as well as particular features, elements, and advantages thereof, will be elucidated in, or be apparent from, the following description and the accompanying drawing figures.

DISCLOSURE OF INVENTION

The present invention achieves the above objects, among others, by providing, in a preferred embodiment, a liquid container, comprising: a housing; a reservoir tube disposed in said housing; a capillary disposed in contact with said reservoir tube; a cap disposed on said housing; and said capillary having an upper portion extending from an upper opening of said cap.

BRIEF DESCRIPTION OF DRAWINGS

Understanding of the present invention and the various aspects thereof will be facilitated by reference to the accompanying drawing figures, provided for purposes of illustration only and not intended to define the scope of the invention, on which:

FIG. 6 is a front elevational view of an opaque reservoir tube of the liquid container.

FIG. 7 is a side elevational view of an opaque reservoir tube of the liquid container.

FIG. 8(A) is an isometric view of an opaque reservoir tube of the liquid container, the reservoir tube being empty.

FIG. 8(B) is an isometric view of a clear reservoir tube of the liquid container, the reservoir tube of the liquid container, the reservoir tube being filled with a porous acetate material.

FIG. 9 is a front elevational view of the capillary of the liquid container.

FIG. 10 is a side elevational view of the capillary of the liquid container.

FIG. 11 is an isometric view of the capillary of the liquid container.

BEST MODE FOR CARRYING OUT THE INVENTION

Figure 1:
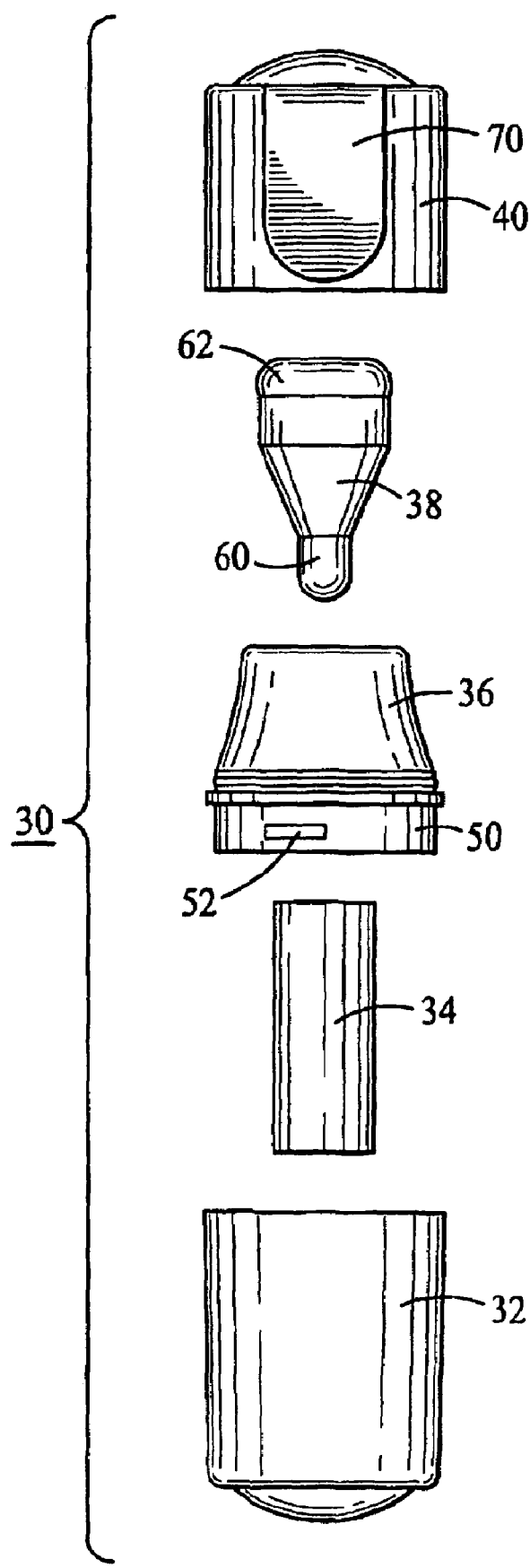
FIG. 1 is an exploded, rear elevational view of a liquid container constructed according to one embodiment of the present invention.

Reference should now be made to the drawing figures on which similar or identical elements are given consistent identifying numerals throughout the various figures thereof, and on which parenthetical references to figure numbers, when used, direct the reader to the view(s) on which the element(s) being described is (are) best seen, although the element(s) may be seen on other figures also.

FIG. 1 illustrates liquid container 30 that includes a bottom 32, a reservoir tube 34, a cap 36, a capillary 38, and a top 40. It will be understood that the foregoing elements of liquid container 30 are frictionally interfitting. Reservoir tube 34 fits into bottom 32. An annular flange 50 formed around the lower end of cap 36 also fits into bottom 32 and is held securely in such position by means of a horizontal ledge 52 which fits into a corresponding horizontal groove formed in the bottom (not shown on FIG. 1). Capillary 38 is inserted into the top of cap 36 and frictionally held therein, the lower end 60 of capillary 38 is plunged into reservoir tube 34, and the upper end 62 of the capillary protrudes from the upper end of the cap. Top 40 includes an optional mounting bracket or clip 70 and the top removably fits over cap 36 and is frictionally held thereon.

Figure 2:
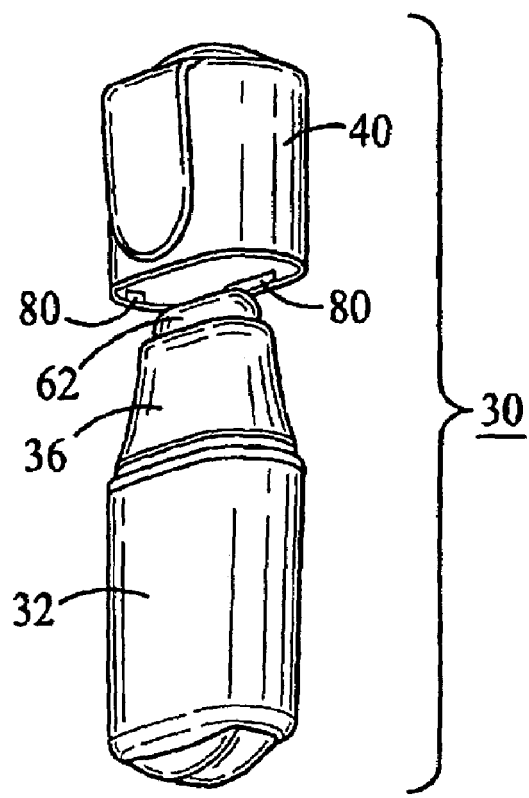
FIG. 2 is an exploded, isometric view of the liquid container, with the cap separated from the other elements of the liquid container.

FIG. 2 illustrates all elements of liquid container assembled, except for top 40 which is shown separated from cap 36. Visible on FIG. 2 are two of the horizontal flanges 80 formed at the lower end of top 40 to grippingly, but removably, hold the top on cap 36.

Figure 3:
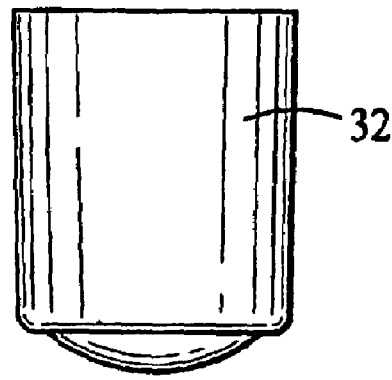
FIG. 3 is a front elevational view of the bottom of the liquid container.
Figure 4:
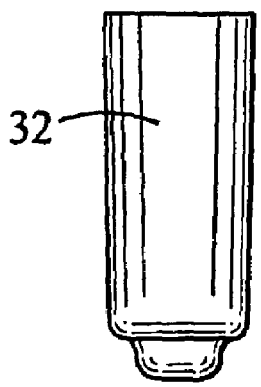
FIG. 4 is a side elevational view of the bottom of the liquid container.
Figure 5:
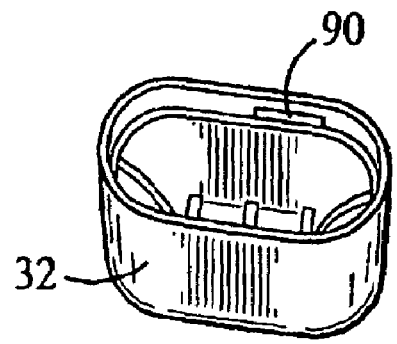
FIG. 5 is an isometric view of the bottom of the liquid container.

FIGS. 3, 4, and 5 are various views of bottom 32. On FIG. 5 is visible horizontal groove 90 into which fits horizontal ledge 52 (FIG. 1).

FIGS. 6, 7, and 8(A) are various views of reservoir tube 34, the reservoir tube being opaque and hollow.

FIG. 8(B) is an isometric view of reservoir tube 34', the reservoir tube being formed of a clear plastic material and filled with a porous acetate material 35.

FIGS. 9, 10, and 11 are various views of capillary 38.

Figure 12:
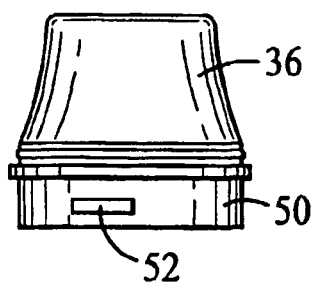
FIG. 12 is a front elevational view of the top of the liquid container.
Figure 13:
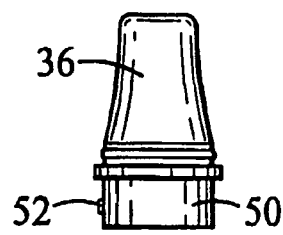
FIG. 13 is a side elevational view of the top of the liquid container.
Figure 14:
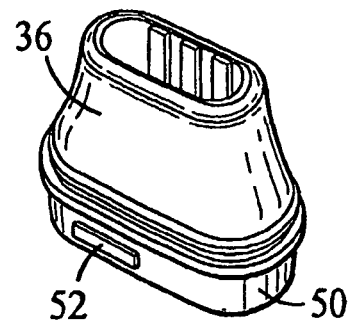
FIG. 14 is an isometric view of the top of the liquid container.

FIGS. 12, 13, and 14 are various views of cap 36.

Figure 15:
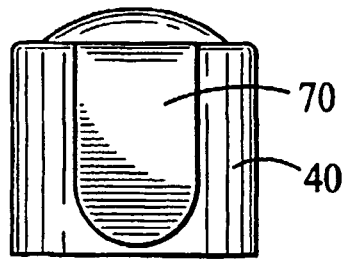
FIG. 15 is a rear elevational view of the cap of the liquid container.
Figure 16:
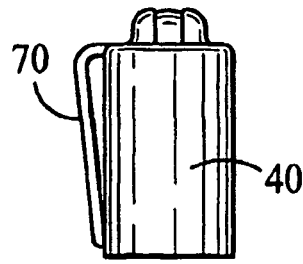
FIG. 16 is a side elevational view of the cap of the liquid container.
Figure 17:
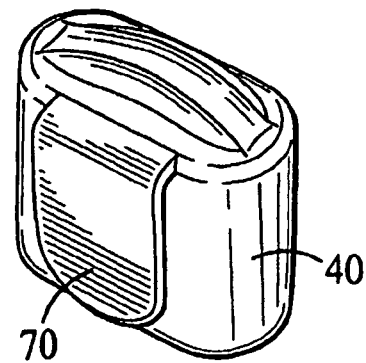
FIG. 17 is an isometric view of the cap of the liquid container.

FIGS. 15, 16, and 17 are various views of top 40.

Figure 20:
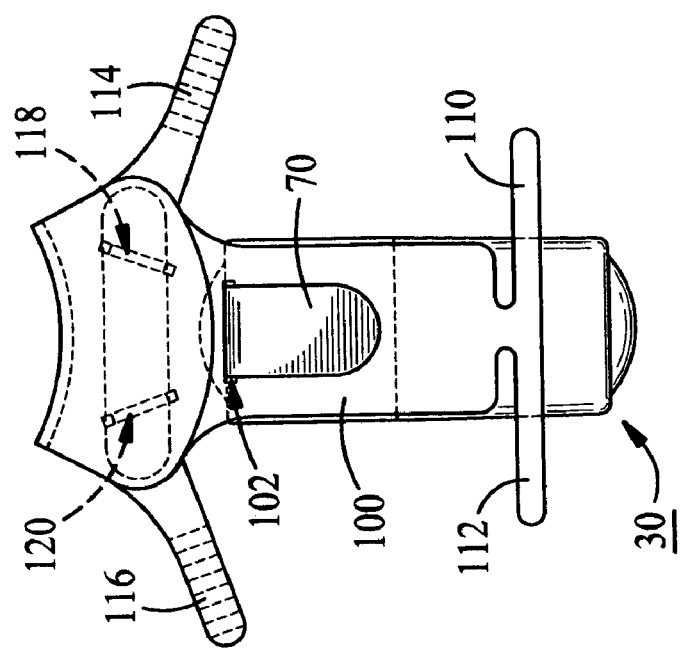
FIG. 20 is a rear elevational view of a mounting yoke/clamp with a liquid container mounted thereon.
Figure 19:
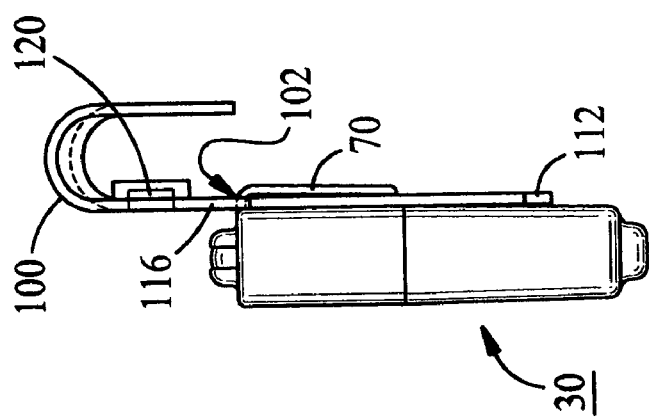
FIG. 19 is a side elevational view of a mounting yoke/clamp with a liquid container mounted thereon.
Figure 18:
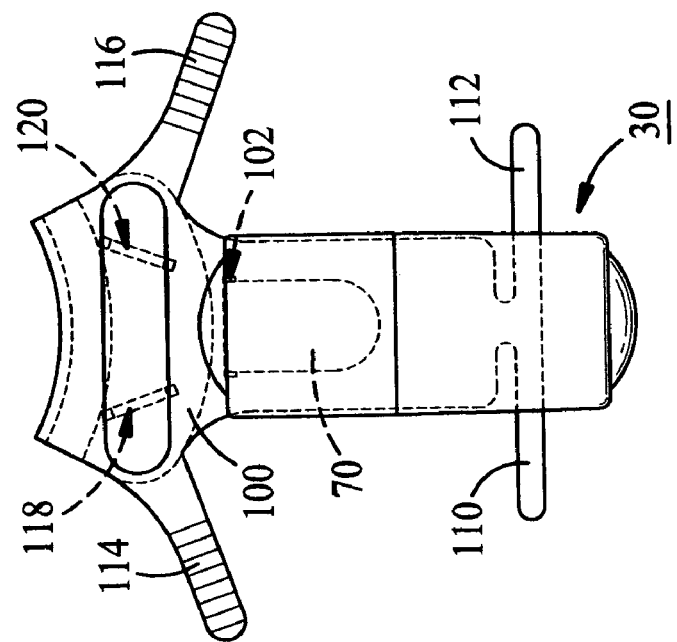
FIG. 18 is a front elevational view of a mounting yoke/clamp with a liquid container mounted thereon.

FIGS. 18, 19, and 20 are various views of a mounting yoke/clamp 100 designed to hold liquid container on a stethoscope (not shown on FIGS. 18, 19, or 20), with the liquid container mounted thereon by means of the insertion of mounting bracket 70 into a horizontal slot 102 defined through the mounting yoke/clamp 100. Two lower arms 110 and 112, extending from the body of mounting yoke/clamp 100, are to be bent around the lower tube of a stethoscope and two upper arms 114 and 116, extending from the body of the mounting yoke/clamp, are serrated, are to be bent around the upper tubes of the stethoscope, and are held in that position by means of the gripping insertion of the upper arms in slots 118 and 120 defined in mounting yoke/clamp 100.

Figures 21A, 21B:
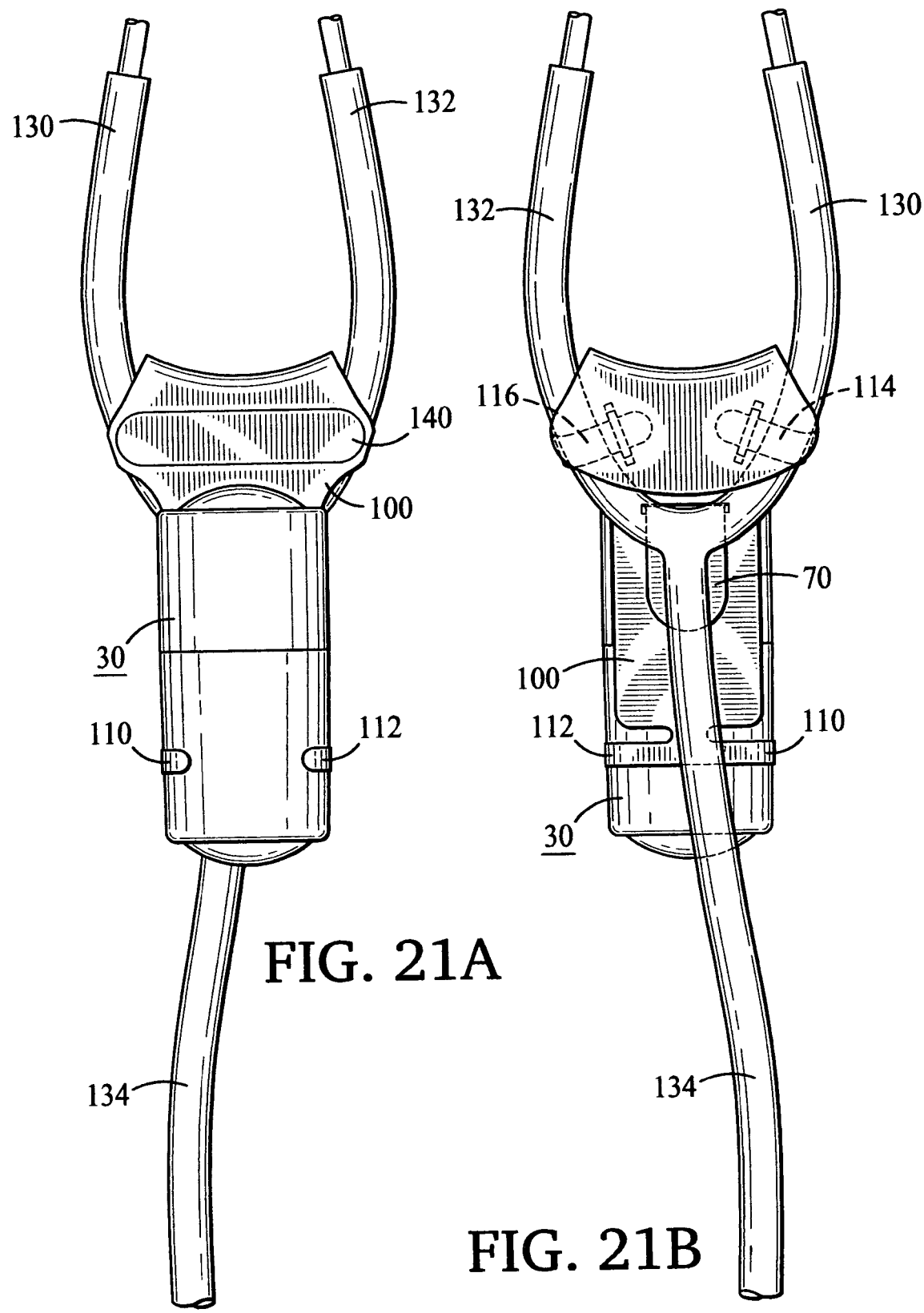
FIG. 21(A) is a fragmentary, front elevational view of the liquid container mounted on a stethoscope using a mounting yoke/clamp.
FIG. 21(B) is a fragmentary, rear elevational view of the liquid container mounted on a stethoscope using a mounting yoke/clamp.

FIGS. 21(A) and 21(B) illustrate liquid container 30 mounted on a stethoscope, the stethoscope having two upper tubes 130 and 132 and a lower tube 134. Also illustrated on Figure is a nameplate that may be provided on mounting yoke/clamp 100.

Figure 22:
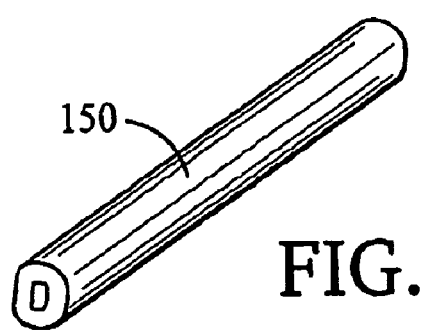

FIG. 22 illustrates a hollow tube 150 into the ends of which lower arms 110 and 112 (FIG. 18) may be inserted to hold the lower arms therein around lower tube 134 (FIG. 21) of the stethoscope.

Figure 23:
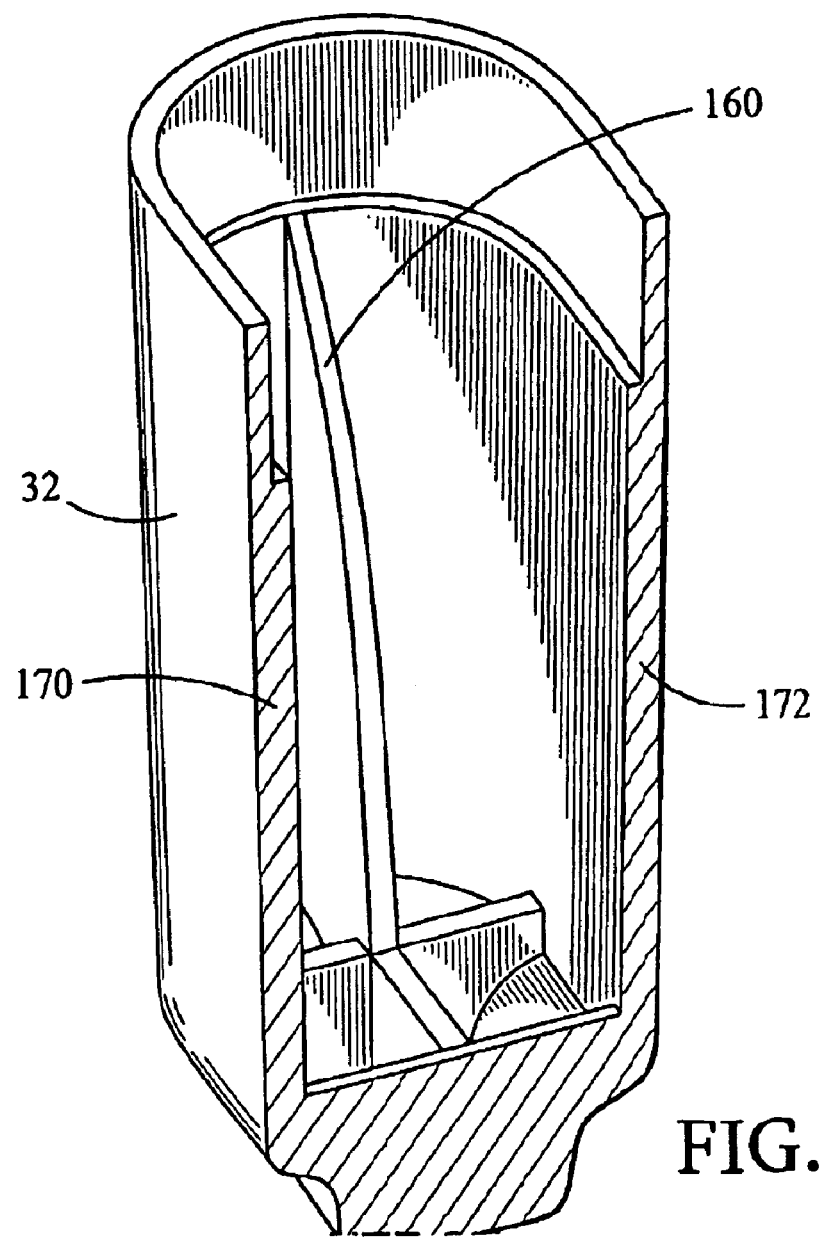
FIG. 23 is an isometric, cutaway view of the bottom of the liquid container.

FIG. 23 illustrates bottom 32 and shows that it includes an internal vertical sloped wall 160. A similar sloped wall (not shown) is provided on the opposite side of bottom 32, the sloped walls being provided to guide reservoir tube 34 (FIG. 1) in place. Reservoir tube 34 extends between opposite walls 170 and 172 of bottom 32.

Figure 24:
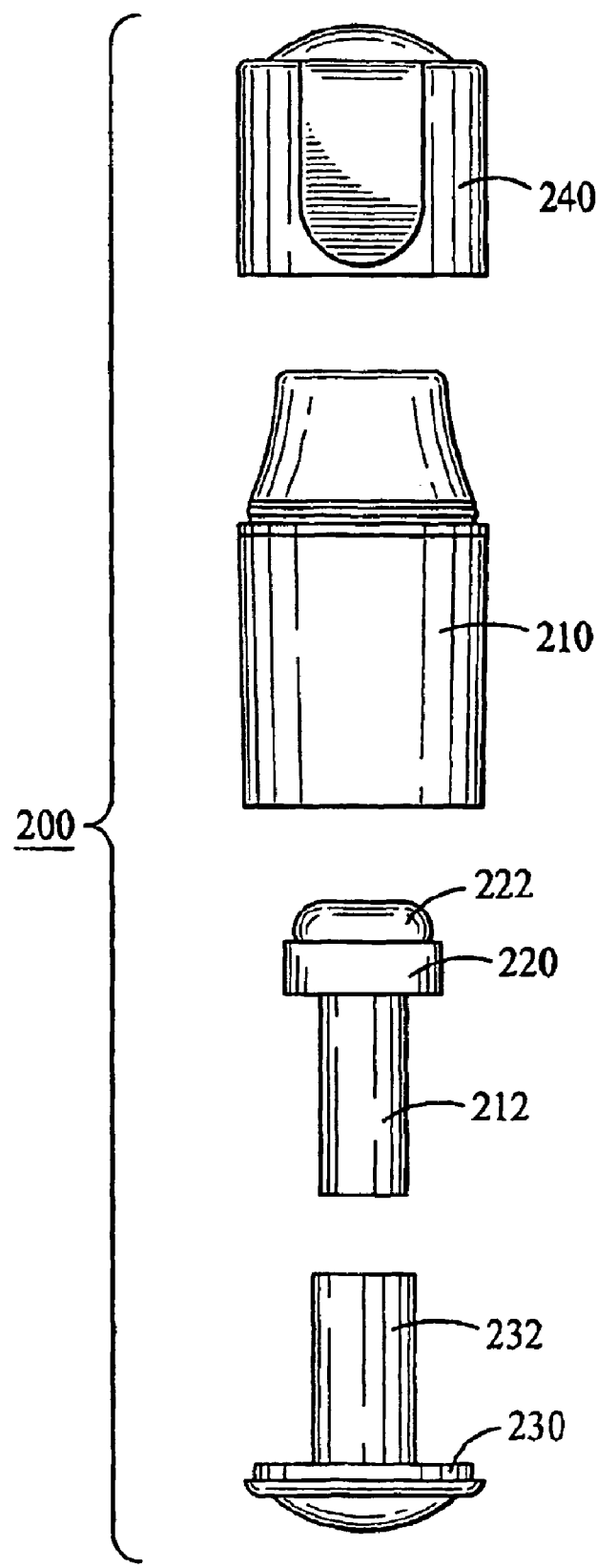
FIG. 24 is an exploded, rear elevational view of a liquid container constructed according to another embodiment of the present invention.

FIG. 24 illustrates a somewhat simplified version of liquid container 30 (FIG. 1), here, a liquid container generally indicated by the reference numeral 200. Cap 36 (FIG. 1) has been lengthened to what may be called a midsection 210 into the bottom of which is inserted a capillary 212. An offset 220 fixedly disposed near the upper end of capillary 212 locates the capillary in midsection 210, with outer edges of the offset engaging inner surfaces of the midsection, and with the top 222 of the capillary extending from the top of midsection 210. Offset 220 prevents capillary 212 from exiting the top of midsection 210. A greatly shortened bottom 230 holding a vertical reservoir 232 snaps onto midsection 210. The means of such attachment may be similar to the horizontal ledge 52 (FIG. 1) and the horizontal groove 90 (FIG. 5) of liquid container 30. Capillary 212 is thrust into reservoir 232. Top 240 is the same as top 40 (FIG. 1).

In use, liquid container 30 (FIG. 1) may be mounted to a stethoscope (FIG. 21) using mounting bracket 70 and mounting yoke/clamp 100 or it may be mounted on another object using suitable mounting means. When liquid container 30 is used to dispense a liquid cosmetic or other material, the mounting means may be omitted. For example, reservoir tube 34 (FIG. 1) may be filled with a disinfectant, such as alcohol, or a liquid cosmetic, or a nail polish remover, or a liquid used in acupuncture, or a liquid used in controlling diabetes, or an insect repellant, as examples of the wide variety of liquids that may be placed in the reservoir tube, depending on final use, and the other elements of liquid container 30 then assembled. When liquid container 30 is to be used, top 40 and cap 36 are separated (FIG. 2), thus exposing top 62 of capillary 60 (FIG. 1). Top 62 of capillary 60 may then be used to sterilize the diaphragm and chestpiece and/or the earpieces of a stethoscope, if reservoir tube 34 (FIG. 1) is filled with alcohol, or used to apply a liquid cosmetic or one of the other materials noted above, to one or more body parts, depending on with what the reservoir tube is filled. Top 40 and cap 36 are then reassembled. Liquid container 200 (FIG. 24) may be similarly mounted and/or used.

Bottom 32, cap 36, and top 40 of liquid container 30 (FIG. 1) and bottom 230, midsection 210, and top 240 of liquid container 200 may be formed of any suitable thermoplastic material. Reservoir tubes 34 (FIG. 1) and 232 (FIG. 24) may be formed of a clear extruded plastic filled with a porous acetate material that is saturated with a disinfectant, such as alcohol, or a liquid cosmetic, or other liquid material. Capillaries 38 (FIG. 1) and 212 (FIG. 24) may be formed of a porous high density polyethylene material. Mounting yoke/clamp 100 (FIG. 18) may be formed of neoprene. Tube 150 (FIG. 22) may be formed of a foamed plastic material. Other materials compatible with the liquid(s) to be placed in reservoir tubes 34 and 232 may be employed as well.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "above", "below", "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction and method without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

The embodiments of the invention in which an exclusive property or privilege is claimed are defined as follows:

1. A liquid container, comprising:
   (a) a bottom;
   (b) a reservoir tube disposed in said bottom;
   (c) a capillary disposed in contact with said reservoir tube;
   (d) a middle portion disposed on said bottom;
   (e) said capillary having an upper portion extending from an upper opening of said middle portion;
   (f) a top removably disposed on said middle portion and sealing in said top said upper portion of said capillary;
   (g) said top removably held on said middle portion by means of at least one flange formed on said top, said at least one flange grippingly engaging said middle portion;
   (h) a mounting clip fixedly disposed on said top, said mounting clip adapted to hold said container on a stethoscope, said mounting clip being formed of neoprene and including two upper arms adapted to be bent around upper tubes of said stethoscope; and two lower arms adapted to be bent around a lower tube of said stethoscope; and
   (i) a hollow tube into the ends of which said lower arms are inserted after they are bent around a lower tube of said stethoscope.

2. A liquid container, comprising:
   (a) a bottom;
   (b) a reservoir tube disposed in said bottom;
   (c) a capillary disposed in contact with said reservoir tube;
   (d) a middle portion disposed on said bottom;
   (e) said capillary having an upper portion extending from an upper opening of said middle portion;
   (f) a top removably disposed on said middle portion and sealing in said top said upper portion of said capillary;
   (g) said top removably held on said middle portion by means of at least one flange formed on said top, said at least one flange grippingly engaging said middle portion;
   (h) a mounting clip fixedly disposed on said top, said mounting clip adapted to hold said container on a stethoscope, said mounting clip being formed of neoprene and including two upper arms adapted to be bent around upper tubes of said stethoscope; and two lower arms adapted to be bent around a lower tube of said stethoscope; and
   (i) a hollow tube formed of a foamed plastic material into the ends of which said lower arms are inserted after they are bent around a lower tube of said stethoscope.

3. A liquid container, comprising:
   (a) a bottom;
   (b) a reservoir tube disposed in said bottom;
   (c) a capillary disposed in contact with said reservoir tube;
   (d) a middle portion disposed on said bottom;
   (e) said capillary having an upper portion extending from an upper opening of said middle portion; and
   (d) said capillary transporting liquid from said reservoir tube to an upper portion of said capillary without being subjected to an intermediate storage member.

4. A liquid container, as defined in claim 3, further comprising: a top removably disposed on said middle portion and sealing in said top said upper portion of said capillary.

5. A liquid container, as defined in claim 4, wherein: said top is removably held on said middle portion by means of at least one flange formed on said top, said at least one flange grippingly engaging said middle portion, said at least one flange not extending around said top.

6. A liquid container, as defined in claim 4, further comprising: a mounting clip fixedly disposed on said top.

7. A liquid container, as defined in claim 6, wherein: said mounting clip is adapted to hold said container on a stethoscope.

8. A liquid container, as defined in claim 7, wherein: said mounting clip includes:
   (a) two upper arms adapted to be bent around upper tubes of said stethoscope; and
   (b) two lower arms adapted to be bent around a lower tube of said stethoscope.

9. A liquid container, as defined in claim 8, further comprising: a hollow tube into the ends of which said lower arms are inserted after they are bent around a lower tube of said stethoscope.

10. A liquid container, as defined in claim 9, wherein: said hollow tube is formed of a foamed plastic material.

11. A liquid container, as defined in claim 6, wherein: said mounting clip is formed of neoprene.

12. A liquid container, as defined in claim 3, wherein: said middle portion fits into said bottom and is held therein by means of a horizontal ledge formed on said middle portion that fits into a corresponding horizontal groove defined in said bottom, said horizontal ledge not extending around said middle portion.

13. A liquid container, as defined in claim 3, wherein: said reservoir tube is formed of a clear plastic material filled with a porous acetate material.

14. A liquid container, as defined in claim 3, wherein: said capillary is formed of a porous high density polyethylene material.

15. A liquid container, as defined in claim 3, wherein: said bottom includes two vertical, oppositely disposed walls sloping from an upper point near a top of said bottom where they have no width to a lower point near a bottom of said bottom to guide said reservoir tube in place.

16. A liquid container, as defined in claim 15, wherein: said reservoir tube is partially held in place by two, oppositely disposed vertical walls of said bottom.

* * * * *